United States Patent [19]
Hodge

[11] Patent Number: 5,252,621
[45] Date of Patent: Oct. 12, 1993

[54] SUPPORTS FOR ACTIVE ENTITIES

[75] Inventor: John C. W. Hodge, Richmond, England

[73] Assignee: Tioxide Group Services Limited, London, England

[21] Appl. No.: 723,917

[22] Filed: Jul. 1, 1991

[30] Foreign Application Priority Data

Jul. 2, 1990 [GB] United Kingdom ............... 9014689

[51] Int. Cl.$^5$ ............................ C08J 9/26; C08J 9/28; C08K 7/22; C08L 67/06
[52] U.S. Cl. ..................................... 521/65; 521/61; 521/62; 521/63; 521/64; 523/220; 523/221; 523/500; 523/502
[58] Field of Search ............... 523/220, 221, 500, 502; 521/61, 62, 63, 64, 65

[56] References Cited

U.S. PATENT DOCUMENTS

| | | | |
|---|---|---|---|
| 3,255,127 | 6/1966 | Von Bonin et al. | 521/64 |
| 3,734,867 | 5/1973 | Will | 521/64 |
| 3,763,056 | 10/1973 | Will | 521/64 |
| 3,822,224 | 7/1974 | Gillan et al. | 521/62 |
| 3,879,314 | 4/1975 | Gunning | 521/62 |
| 4,007,142 | 2/1977 | Clarke et al. | 524/44 |
| 4,043,869 | 8/1977 | Barker et al. | 530/391.1 |
| 4,273,830 | 6/1981 | Gillan et al. | 521/62 |
| 4,314,033 | 2/1982 | Gillan et al. | 521/65 |
| 4,321,332 | 3/1982 | Beresford et al. | 523/505 |
| 4,363,888 | 12/1982 | Willison et al. | 523/502 |
| 4,461,848 | 7/1984 | Lawson et al. | 521/64 |
| 4,461,849 | 7/1984 | Karickhoff | 521/63 |
| 4,483,945 | 11/1984 | Beresford et al. | 521/64 |
| 4,489,174 | 12/1984 | Karickhoff | 521/64 |
| 4,522,953 | 6/1985 | Barby et al. | 521/64 |
| 4,808,633 | 2/1989 | Ferguson et al. | 521/64 |
| 4,826,881 | 5/1989 | Ferguson et al. | 521/64 |
| 4,839,395 | 6/1989 | Masamizu et al. | 521/64 |
| 4,917,765 | 4/1990 | Ferguson et al. | 162/168.2 |
| 5,055,513 | 10/1991 | Banford et al. | 524/423 |

FOREIGN PATENT DOCUMENTS

| | | |
|---|---|---|
| 481144 | 3/1976 | Australia . |
| 3522287 | 1/1987 | Fed. Rep. of Germany . |
| 1476510 | 6/1977 | United Kingdom . |
| 2225017 | 5/1990 | United Kingdom . |

OTHER PUBLICATIONS

Perry, "Chemical Engineer's Handbook", pp. 754–755 (1950).
Kirk-Othmer *Encyclopedia of Chemical Technology*, 3rd Ed., vol. 15, p. 648 (1981).
Hislop et al., "Microvoid Coatings: Pigmented, Vesiculated Beads in Flat Latex Paints", Journal of Coatings Technology, vol. 50, No. 642, pp. 69–77 (Jul. 1978).
Bierwagen, "Increased Durability in Aircraft Coatings by the Use of Pigmented Polymers Beads", XVth FATIPEC Congres, 3E-Activities, vol. III, 110, 111, 120, 121 (1980).

*Primary Examiner*—Paul R. Michl
*Assistant Examiner*—Peter Szekely
*Attorney, Agent, or Firm*—Millen, White, Zelano & Branigan

[57] ABSTRACT

A polymeric bead has now been developed to act as a support for other entities having a volume mean diameter of up to 250 microns and having a surface provided with pores which form at least 10% by area of the surface. At least one third of the total area of the pores is provided by pores having a larger size of at least 0.4 micron. A method for the manufacture of such polymeric beads involves using a water-in-oil-in-water emulsion technique in which the amount of water used in the preparation of the aqueous phase is not greater than 125 parts by weight per 265 parts by weight of the mixture of the polyester resin and monomer which is used.

The porous beads provide an excellent base for carrying enzymes, bacteria and catalysts species useful in a wide range of applications.

15 Claims, No Drawings

SUPPORTS FOR ACTIVE ENTITIES

This invention relates to products suitable for use as supports for active entities and particularly to supports for biologically active species such as bacteria.

There has been an increasing use over the recent past in the use of biologically active species, such as bacteria to treat other materials to effect changes in, or purification of, materials such as water. Small sized biologically active species can be difficult to retain in, say, a treatment column or other vessel through which a fluid passes and there is a need for a means of locating such entities within a treatment or reaction zone in an effective manner.

According to the invention a product suitable for use as a carrier for an active entity comprises a vesiculated polymer bead having a volume mean diameter of up to 250 microns and having a surface with pores which form at least 10% by area of the surface and at least one third of the total area of said pores being contributed by pores having a largest size of at least 0.4 micron.

According to the invention also a process for the manufacture of vesiculated polymer beads comprises mixing:

an oil phase (A) comprising a cross-linkable water-insoluble carboxyl containing polyester resin in solution with a monomer copolymerisable therewith, with an aqueous phase (B) comprising an emulsifying agent in aqueous solution in which the weight of water (X) is not greater than 125 parts by weight per 265 parts of said polyester resin and said monomer to produce a water-in-oil emulsion (C), mixing said emulsion (C) with a further aqueous phase D to produce a water-in-oil-in-water emulsion (E) containing a total amount of water (Y) and in which the amount of water (X) is up to 12.6% by weight of the total amount of water (Y) and cross-linking the resin in said globules to form a dispersion of vesiculated polymer beads.

In the specification the term largest size refers to the greatest dimension (diameter) of the pore and when the pore is circular then size will be the diameter.

From the pores chambers or voids can extend into the body of the bead which can interconnect with other chambers or voids in the bead. Preferably the beads have pores forming from 20 to 70 per cent of the area of the surface, more preferably from 30 to 60 per cent of the surface.

The surface area of the beads is substantially greater than that of solid beads of the same size distribution. The surface area can be up to 500 times that of such solid beads and conveniently is at least 20 times. High surface area is preferred for use in catalyst supports.

In the products of the invention at least one third of the total area of said pores is contributed by pores having a largest size of at least 0.4 micron. Preferably at least one half of the total area is contributed by said pores.

The beads can have diameters of up to 250 microns expressed as volume mean diameter but usually will be less than 100 microns in volume mean diameter. Very small beads can be used such as those having a size of 2 microns.

Whilst the size of the pores does depend to some extent on the bead size it is necessary to choose a pore size that is appropriate for the active entity to be carried. These entities can vary greatly in size, typically from 1 to 10 microns.

Generally speaking the nature of the polymer used to form the bead is not critical provided due regard is taken of the final use of the beads. The polymer can be a polyester, obtained by condensation of a polycarboxylic acid and a polyol, a polyester amide, a polyurethane, a urea-aldehyde resin, a cellulosic ester or any other suitable material.

Preferably the beads are formed from an unsaturated polyester resin cross-linked with unsaturated monomer and the polyester resin used may be any such resin which is capable of reaction with an unsaturated organic monomer at temperatures below about 100° C. to form a rigid cross-linked polymer having suitable physical and chemical properties for bead formation. It is preferred, in the process of the present invention, to use resins formed by the condensation of a dihydric alcohol (or its corresponding epoxide) with a proportion of an aliphatic dicarboxylic acid and with a proportion of an aromatic dicarboxylic acid (or the corresponding anhydrides).

Unsaturated polyester resins formed from the condensation of ethylene, propylene, tetra-, penta- or hexamethylene glycols, or their corresponding epoxides, with unsaturated dibasic acids such as fumaric or maleic (or the anhydride in the latter case) and with a proportion of an aromatic acid such as isophthalic or phthalic and (or phthalic anhydride) have been found to be particularly suitable for the present process. The condensation product of propylene glycol, fumaric acid or maleic anhydride and phthalic acid (or the anhydride) is particularly suitable.

It is generally desirable that the proportions of components and the degree of condensation be such that the resulting unsaturated polyester resin has an acid value in the range 5 to 100 (expressed as mgms KOH per gram of resin) and particularly one in the range 10 to 35.

It has also been found advantageous to utilise unsaturated polyester resins having a viscosity in the range 5 to 60 and particularly a viscosity in the range 20 to 40 poise, (when measured as a 70% by weight solution in the unsaturated monomer, e.g. styrene, at 25° C.).

It may also be of advantage to modify the unsaturated polyester resin by the incorporation into the resin of polyethylene oxide chains since such resins may also form stable emulsions of the type required by the present invention.

In the manufacture of the beads of this invention the polyester resin is initially dissolved in the unsaturated monomer to produce an oil phase (A), the latter being present in sufficient quantity to provide the necessary cross-linking of the resin component. The amount of monomer present is normally at least 30% by weight of the weight of resin and is preferably present in an amount from 40% to 70%.

The unsaturated monomer in which the resin is dissolved will be substantially insoluble in water and as indicated is capable of copolymerising with the resin to produce a cross-linked product. Generally the unsaturated monomer is an unsaturated aromatic hydrocarbon and preferably is a vinyl aromatic hydrocarbon such as styrene, divinyl benzene, alpha-methyl styrene or the mixed monomers available commercially as vinyl toluene. If desired an unsaturated aliphatic co-monomer can be mixed with the unsaturated monomer and typical co-monomers are the esters of acrylic or methacrylic acids such as methyl acrylate, methyl methacrylate, ethyl acrylate and n-butyl acrylate and other polymerisable compounds such as acrylonitrile, vinyl acetate and ethylene glycol dimethacrylate.

If desired the solution of the resin in the monomer may also contain a pigment such as titanium dioxide or as desired any other pigment, filler or extender in an amount of up to 70 weight per cent on weight of solution, and preferably of up to 55% by weight.

An aqueous phase (B) is prepared which comprises an emulsifying agent in aqueous solution. The emulsifying agent has the function of stabilising water-in-oil type emulsions and examples of suitable agents are alkyl phenol ethoxylate sulphate salts and alkyl phenol ethoxylate phosphate salts.

In the process used to manufacture the beads of the present invention the amount of water (X) present in the aqueous phase B is reduced substantially from that amount which has been present in processes employed to manufacture beads of conventional structure having surface pores. In the process of this invention the amount of water in the aqueous phase B does not exceed 125 parts by weight per 265 parts by weight of the resin and said monomer and usually is from 10 to 100 parts per 265 parts this resin solution preferably from 15 to 30 parts.

The oil phase (A) and the aqueous phase (B) are then mixed to produce a water-in-oil emulsion (C).

A further aqueous phase (D) is usually prepared to provide the necessary final addition of water and any other ingredients such as thickeners and stabilisers. The total amount of water employed is similar to that which has been used in prior processes but in this process the amount of water (X) present in the first aqueous phase (B) is up to 12.6% by weight of the total (Y) present in the final emulsion (E) usually from 1.6% to 10.2% by weight and preferably from 2.1% to 3.5% by weight of the total weight (Y) used.

The water-in-oil emulsion (C) is mixed with the further aqueous phase (D) to produce a water-in-oil-in-water system containing the oil (resin and monomer) globules which on polymerisation produce the beads of the invention.

The resin is cross-linked by copolymerising the chosen monomer with the resin. Initiation of polymerisation is usually effected chemically by the addition to the emulsion of a suitable initiator such as an organic peroxide, e.g. cumene hydroperoxide. If desired, and usually, the polymerisation is effected in the presence of an accelerator such as cobalt naphthenate which can conveniently be added to the oil phase (A) prior to mixing with the aqueous phase (B).

Polymerisation is usually effected at an elevated temperature of greater than 40° C. and usually temperatures within the range 50° C. to 65° C. will be employed. For maximum polymerisation and cross-linking it is desirable that the dispersion of beads be aged. Desirably the amount of free monomer in the dispersion of the beads after completion of the process should be below 1% by weight of the dispersion and preferably below 0.3% by weight.

The products of the present invention are of use as supports for active entities and such entities can be catalysts or catalyst components such as catalysts based on transitional metal oxides of vanadium pentoxide for use in organic oxidation reactions. The supports are ideally suitable for use as carriers for biological active entities such as enzymes e.g. pullalanase, carboxy peptidase, dextranase or papain. Bacteria may also be carried by the supports of the invention and find use in a wide variety of processes. Also the porous beads can be used in applications where slow-release of an entity is needed e.g. an emollient oil. The products also can be used as chromatography supports in such techniques as high performance liquid chromatography, gas liquid chromatography and size extrusion chromatography. Also the products can be used as supports for the solid-phase synthesis of peptides and oligonucleotides.

The invention is illustrated in the following Examples. Example I is a comparative Example showing the standard production process for beads. In these Examples all "parts" are parts by weight.

EXAMPLE 1 (Standard)

An unsaturated polyester resin was prepared by condensing together maleic anhydride, phthalic anhydride and propylene glycol in the molar ratio 3:1:4.5. The product had an acid value of 16 mg KOH per gram of solid resin.

Into 179 parts of a 59% weight solids solution of the above resin in styrene was milled 0.75 parts of magnesium oxide until they were thoroughly dispersed (around 30 minutes). To this mixture was added 86 parts of styrene and 20 parts of hot water (around 80° C.), and milling was continued for 1 minute. This oil phase was then left to stand for one hour.

Separately, 9.5 parts of a 90% weight solids aqueous solution of an ammonium nonylphenol ethoxylate sulphate surfactant were mixed with 2.85 parts of industrial methylated spirits and 6.65 parts of water. This was milled with 155 parts of water at 50° C. and, 0.1 part of an antifoaming agent to give an aqueous phase.

The above aqueous phase was slowly added to the oil phase with stirring, and the mixture was milled for 10 minutes to give a water-in-oil emulsion. 136 parts of this was immediately added to a further aqueous phase, containing 5 parts of a 1.5% weight solids solution of hydroxyethyl cellulose thickener, 30 parts of a 7.5% weight solids solution of polyvinylalcohol (as stabiliser) and 215 parts of water, and was milled for 2 minutes, at which point a water-in-oil-in-water system had formed, with the oil globules averaging around 4 microns in diameter in which (X) is 15.5% of (Y) total amount of water.

84 parts of hot water were then added, with minimum possible milling, formed by 2 parts of a 1% aqueous ferrous sulphate solution, 10 parts of a 3.0% aqueous diethylene triamine solution and 0.5 parts of cumene hydroperoxide. The slurry was kept at 50° C. overnight to ensure complete curing of the unsaturated polyester. This gave a 17.2% weight solids slurry of cross-linked polyester resin beads.

The product of Example I was a polymeric bead having surface pores of size of from 0.05 to 0.3 micron which covered about 3% to 5% of the surface area of the bead.

EXAMPLE 2

An unsaturated polyester resin was prepared by condensing together maleic anhydride, phthalic anhydride and propylene glycol in the molar ratio 3:1:4.5. The product had an acid value of 16 mg KOH per gram of solid resin.

Into 179 parts of a 59% weight solids solution of the above resin in styrene was milled 0.75 parts of magnesium oxide until they were thoroughly dispersed (around 30 minutes). To this mixture was added 86 parts of styrene and 20 parts of hot water (around 80° C.), and milling was continued for 1 minute. This oil phase was then left to stand for one hour.

Separately, 9.5 parts of a 90% weight solids aqueous solution of an ammonium nonylphenol ethoxylate sulphate surfactant were mixed with 2.85 parts of industrial methylated spirits and 6.65 parts of water. This was milled with 25 parts of water at 50° C. and 0.1 part of an antifoaming agent to give an aqueous phase.

The above aqueous phase was slowly added to the oil phase with stirring, and the mixture was milled for 10 minutes to give a water-in-oil emulsion. 99 parts of this was immediately added to a further aqueous phase, containing 5 parts of a 1.5% weight solids solution of hydroxyethyl cellulose thickner, 30 parts of a 7.5% weight solids solution of polyvinylalcohol (as stabiliser) and 252 parts of water, and was milled for 2 minutes, at which point a water-in-oil-in-water system had formed, with the oil globules averaging around 5 microns in diameter in which (X) was 3.26% of (Y).

84 parts of hot water were then added, with minimum possible milling, followed by 2 parts of a 1% aqueous ferrous sulphate solution, 10 parts of a 3.0% aqueous diethylene triamine solution and 0.5 parts of cumene hydroperoxide. The slurry was kept at 50° C. overnight to ensure complete curing of the unsaturated polyester. This gave a 17.2% weight solids slurry of cross-linked polyester resin beads.

The products of Example 2 had pores of size of from 0.2 micron to 1.2 microns which covered 38% to 51% of the surface of the beads.

EXAMPLE 3

An unsaturated polyester resin was prepared by condensing together maleic anhydride, phthalic anhydride and propylene glycol in the molar ratio 3:1:4.5. The product had an acid value of 16 mg KOH per gram of solid resin.

Into 920 parts of a 57.4% weight solids solution of the above resin in styrene was milled 3.75 parts of magnesium oxide until they were thoroughly dispersed (around 30 minutes). To this mixture was added 405 parts of styrene and 100 parts of hot water (around 80° C.), and milling was continued for 1 minute. This oil phase was then left to stand for one hour.

Separately, 9.5 parts of a 90% weight solids aqueous solution of an ammonium nonylphenol ethoxylate sulphate surfactant were mixed with 2.85 parts of industrial methylated spirits and 6.65 parts of water. This was milled with 25 parts of water at 50° C. and 0.01 part of an antifoaming agent to give an aqueous phase.

The above aqueous phase was slowly added to 300 parts of the oil phase with stirring, and the mixture was milled for 10 minutes to give a water-in-oil emulsion. 99 parts of this was immediately added to a further aqueous phase, containing 15 parts of a 7.5% by weight solution of polyvinylalcohol (as stabiliser) and 252 parts of water, and was milled for 2 minutes, at which point a water-in-oil-in-water system had formed, with the oil globules averaging around 20 microns in diameter, in which (X) was 3.4% of (Y).

84 parts of hot water were then added, with minimum possible milling, followed by 5 parts of a 1% aqueous ferrous sulphate solution, 20 parts of a 3.0% aqueous diethylene triamine solution and 1.0 parts of cumene hydroperoxide. The slurry was kept at 50° C. overnight to ensure complete curing of the unsaturated polyester. This gave a slurry of cross-linked polyester resin beads.

The products of Example 3 had pores of size of from 0.2 microns to 1.8 microns, which covered 10% to 36% of the surface of the beads. Mercury intrusion porosimetry indicated a surface area of 64 m$^2$ per gram, compared with a theoretical value for solid beads of that size range of around 0.2 m$^2$ per gram.

I claim:

1. A product suitable for use as a carrier for an active entity comprising a vesiculated polymer bead formed of a polymer selected from the group consisting of a polyester, polyester amide, polyurethane, urea-aldehyde resin, and cellulosic ester, each having a volume mean diameter of up to 250 microns and having a surface with surface pores which form 20% to 70% by area of the surface and at least one-third of the total area of said surface pores being contributed by surface pores having a largest size of at least 0.4 micron.

2. A product according to claim 1 in which the beads have a volume mean diameter of less than 100 microns.

3. A product according to claim 1 in which at least one half of the total area of said surface pores is contributed by surface pores having a largest size of at least 0.4 micron.

4. A product according to claim 1 in which the polymer is crosslinked by a substantially water-insoluble unsaturated monomer.

5. A process for the manufacture of vesiculated polymer beads comprising mixing:
   an oil phase (A) comprising a crosslinkable water-insoluble carboxyl containing polyester resin in solution with a monomer copolymerizable therewith, with
   an aqueous phase (B) comprising an emulsifying agent in aqueous solution in which the weight of water (X) is from 15 to 30 parts by weight per 265 parts by weight of said polyester resin and said monomer to produce a water-in-oil emulsion (C), mixing said emulsion (C) with
   a further aqueous phase (D) to produce a water-in-oil-in-water emulsion (E) containing a total amount of water (Y) and in which the amount of water (X) is from 1.6 to 10.2% by weight of the total amount of water (Y) and
   cross-linking the resin in said emulsion (E) to form a dispersion of vesiculated polymer beads.

6. The process of claim 5 wherein the amount of the monomer in oil phase (A) is at least 30% by weight of the resin.

7. The process of claim 5 wherein the polyester resin is selected from the class consisting of condensation products of at least one dihydric alcohol, at least one aliphatic carboxylic acid and at least one aromatic dicarboxylic acid.

8. The process of claim 5 wherein the oil phase (A) contains a pigment in an amount of up to 70% by weight of the oil phase.

9. The process of claim 5 wherein the amount of water (X) is from 2.1 to 3.5% by weight of (Y).

10. The process of claim 5 wherein the crosslinking of the resin with said monomer is effected at a temperature greater than 40° C.

11. A process for the manufacture of vesiculated polymer beads comprising mixing:
    an oil phase (A) comprising a crosslinkable water-insoluble carboxyl containing polyester resin in solution with a monomer copolymerizable therewith, with an aqueous phase (B) comprising an emulsifying agent in aqueous solution in which the weight of water (X) is from 10 to 100 parts by weight per 265 parts by weight of said polyester resin and said monomer to produce a water-in-oil emulsion (C), mixing said emulsion (C) with a further aqueous phase (D) to produce a water-in-oil-in-water emulsion (E) containing a total amount of water (Y) and in which the amount of water (X) is from 2.1 to 3.5% by weight of the total amount of water (Y) and crosslinking the resin in said emulsion (E) to form a dispersion of vesiculated polymer beads.

12. The process of claim 11 wherein the amount of the monomer in oil phase (A) is at least 30% by weight of the resin.

13. The process of claim 11 wherein the polyester resin is selected from the class consisting of condensation products of at least one dihydric alcohol, at least one aliphatic carboxylic acid and at least one aromatic dicarboxylic acid.

14. The process of claim 11 wherein the oil phase (A) contains a pigment in an amount of up to 70% by weight of the oil phase.

15. The process of claim 11 wherein the crosslinking of the resin with said monomer is effected at a temperature greater than 40° C.

* * * * *